United States Patent

Zirps et al.

Patent Number: 5,938,678
Date of Patent: Aug. 17, 1999

[54] SURGICAL INSTRUMENT

[75] Inventors: Christopher T. Zirps, Milton; William R. Rebh, Shrewsbury, both of Mass.

[73] Assignee: Endius Incorporated, Plainville, Mass.

[21] Appl. No.: 08/873,283

[22] Filed: Jun. 11, 1997

[51] Int. Cl.⁶ .................................................. A61B 17/32
[52] U.S. Cl. .................... 606/170; 606/167; 606/174; 606/188; 606/205; 606/206; 606/207
[58] Field of Search ................................... 606/170, 174, 606/205, 206, 207, 210, 188, 167

[56] References Cited

U.S. PATENT DOCUMENTS

| | | |
|---|---|---|
| 3,470,876 | 10/1969 | Barchilon . |
| 3,605,725 | 9/1971 | Bentov . |
| 5,437,630 | 8/1995 | Daniel et al. ............................. 606/205 |
| 5,454,827 | 10/1995 | Aust et al. ............................... 606/170 |
| 5,522,788 | 6/1996 | Kuzmak . |
| 5,618,294 | 4/1997 | Aust et al. ............................... 606/174 |
| 5,741,286 | 4/1998 | Recuset .................................. 606/170 |

FOREIGN PATENT DOCUMENTS

| | | |
|---|---|---|
| 0301288A1 | 2/1989 | European Pat. Off. . |
| 2662778 | of 0000 | France . |
| 3920706A1 | 1/1991 | Germany . |
| 4136861A1 | 5/1993 | Germany . |
| 4204051A1 | 8/1993 | Germany . |
| 09300048 | 1/1993 | WIPO . |
| 09304634 | 3/1993 | WIPO . |
| 09320760 | 10/1993 | WIPO . |

*Primary Examiner*—Michael Buiz
*Assistant Examiner*—(Jackie) Tan-Uyen T. Ho
*Attorney, Agent, or Firm*—Tarolli, Sundheim, Covell, Tummino & Szabo

[57] ABSTRACT

A surgical instrument (10) includes a handle (12), a rigid stem section (20) extending from the handle, and a flexible stem section (24) extending from the rigid stem section. A surgical tool (30) connected with a distal end of the flexible stem section (24) includes a movable part (34). The flexible stem section (24) comprises a plurality of relatively pivotable vertebrae (120–129) extending along the flexible stem section and an extension spring (150) extending axially through the plurality of vertebrae for transmitting axial load between the surgical tool (30) and the rigid stem section (20). An actuator cable (180) extends through the extension spring (150) and is connected with the movable tool part (34) for applying force to the movable tool part to move the movable tool part relative to the flexible stem section (24). The extension spring (150) carries the axial load on the flexible stem section (24).

9 Claims, 2 Drawing Sheets

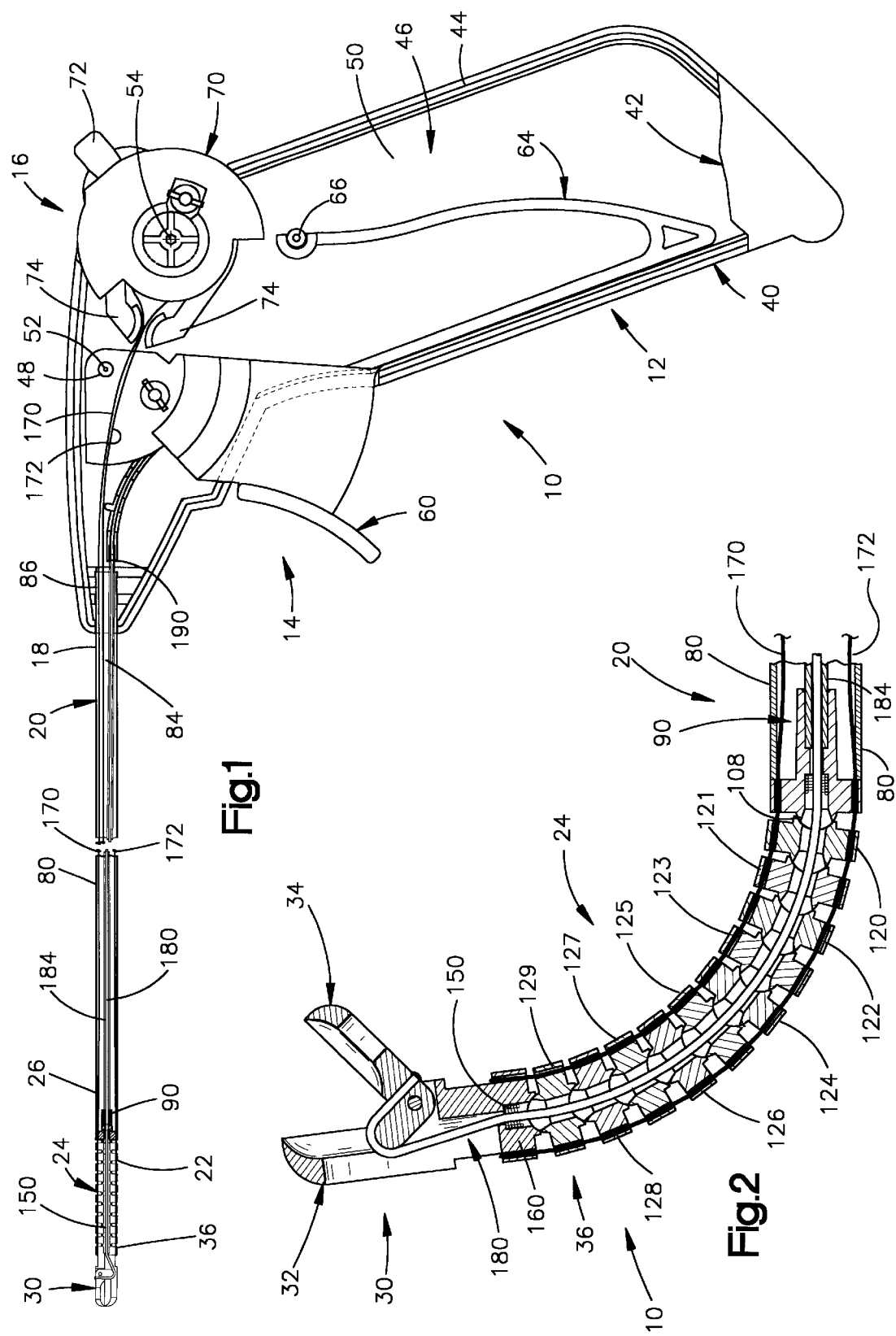

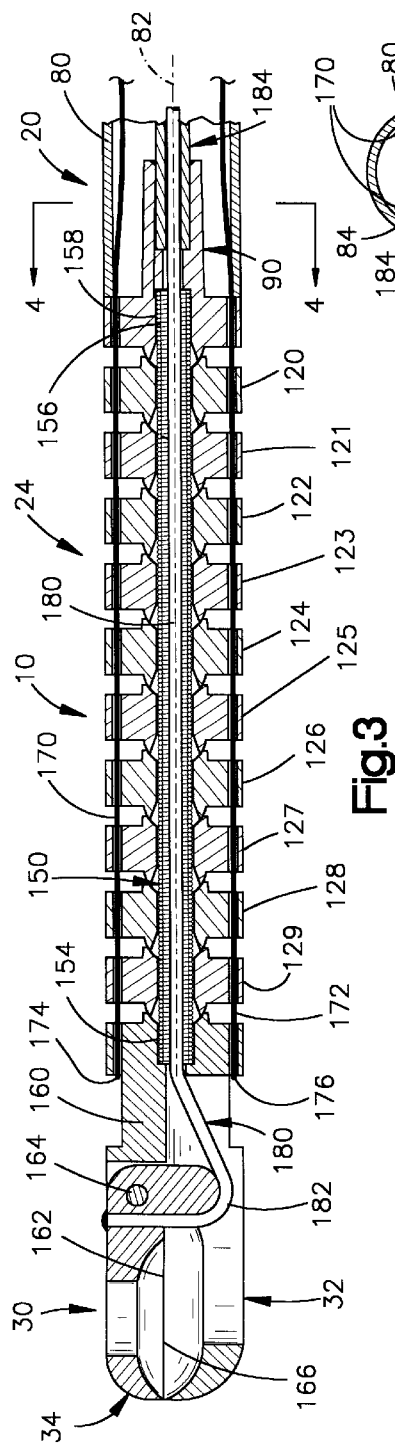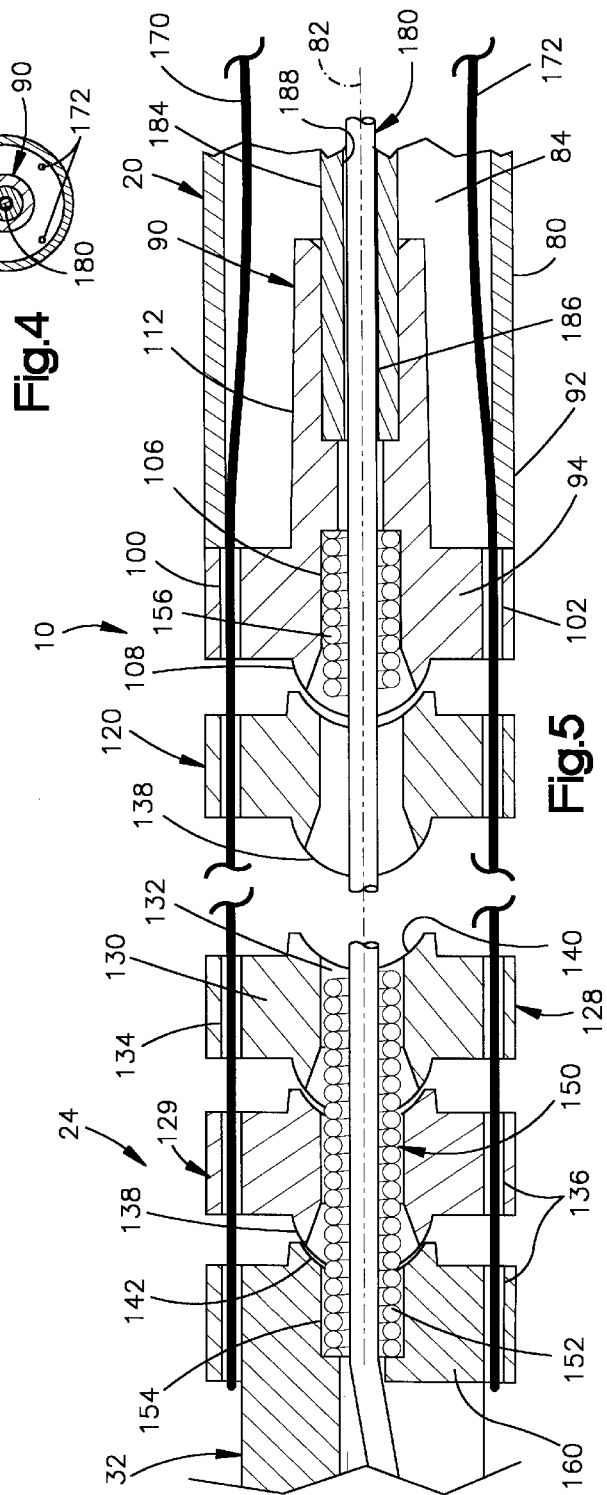

SURGICAL INSTRUMENT

BACKGROUND OF THE INVENTION

The present invention relates to a surgical instrument and, more particularly, to an endoscopic surgical instrument which may be used for cutting and/or removal of tissue.

SUMMARY OF THE INVENTION

The present invention is a surgical instrument including a handle, a rigid stem section extending from the handle, and a flexible stem section extending from the rigid stem section. A surgical tool connected with a distal end of the flexible stem section includes a movable part. The flexible stem section comprises a plurality of relatively pivotable vertebrae extending along the flexible stem section, and an extension spring extending axially through the plurality of vertebrae for transmitting axial load between the surgical tool and the rigid stem section. An actuator cable extends through the extension spring and is connected with the movable tool part for applying force to the movable tool part to move the movable tool part relative to the flexible stem section.

BRIEF DESCRIPTION OF THE DRAWINGS

Further features of the present invention will become apparent to those skilled in the art to which the present invention relates from reading the following specification with reference to the accompanying drawings, in which:

FIG. 1 is a side elevational view, with parts removed, of a surgical instrument constructed in accordance with a first embodiment of the present invention;

FIG. 2 is an enlarged view of a flexible stem section of the surgical instrument of FIG. 1, shown in a bent condition;

FIG. 3 is an enlarged sectional view of the flexible stem section, shown in a linear condition;

FIG. 4 is a view taken along line 4—4 of FIG. 3; and

FIG. 5 is a further enlarged view of portions of FIG. 3.

DESCRIPTION OF A PREFERRED EMBODIMENT

The present invention relates to a surgical instrument and in particular to an endoscopic surgical instrument which may be used for cutting and/or removal of tissue. The present invention is applicable to various surgical instrument constructions. As representative of the present invention, FIG. 1 illustrates a surgical instrument 10.

The surgical instrument 10 includes generally a handle 12 with an actuator assembly 14 and a deflection control assembly 16. A proximal end portion 18 of a first stem section or rigid stem section 20 is fixed to the handle 12. A proximal end portion 22 of a second stem section or flexible stem section 24 is connected with a distal end portion 26 of the rigid stem section 20. A surgical tool 30, including a fixed tool part 32 (FIG. 2) and a movable tool part 34, is located on a distal end portion or tip portion 36 of the flexible stem section 24.

The handle 12 (FIG. 1) of the surgical instrument 10 has a pistol grip configuration which is configured to be manually gripped by a person's hand. The handle 12 includes a first handle part 40 and a second handle part 42 which in overall configuration are substantially mirror images of each other and which are joined together to form the handle. The second handle part 42 is, for clarity, shown only fragmentarily. The second handle part 42, overlies the first handle part 40 and covers the other parts of the surgical instrument 10 which are mounted on the first handle part.

The first handle part 40 has an outer peripheral rim 44 extending around a main wall 46. A trigger pivot pin 48 projects from the inner side surface 50 of the main wall 46 of the first handle part 40. The trigger pivot pin 48 defines a trigger pivot axis 52. A deflection control lever pivot pin 54 projects from the inner side surface 50 of the main wall 46 of the first handle part 40, at a location spaced apart from the trigger pivot pin 48.

The actuator assembly 14 includes a trigger 60. The trigger 60 is supported on the trigger pivot pin 48 for pivotal movement relative to the handle 12 about the pivot axis 52. The trigger 60 extends out of the handle 12 and is manually engageable to effect pivotal movement of the trigger relative to the handle. A generally V-shaped spring 64 formed as one piece with the trigger 60 engages a spring support pin 66 on the first handle part 40. The spring 64 biases the trigger 60 to an unactuated position, as shown in FIG. 1, relative to the handle 12.

The deflection control assembly 16 includes a deflection control lever 70. The deflection control lever 70 is supported on the deflection control lever pivot pin 54 for pivotal movement relative to the handle 12. A manually engageable portion 72 of the deflection control lever 70 projects from the handle 12. A tensioner 74 is disposed between the deflection control lever 70 and the first handle part 12. The tensioner 74 is supported for limited rotation about the pivot pin 54.

It should be understood that the deflection control assembly 16 is illustrated only schematically. Other types of deflection control assemblies can be substituted. Thus, the deflection control assembly 16 is illustrative of the various types of deflection control assemblies which can be used to provide the force for bending the flexible stem section 24 of the surgical instrument 10 in the manner illustrated.

The rigid stem section 20 of the surgical instrument 10 includes a rigid main tube 80 which extends between and interconnects the handle 12 and the flexible stem section 24. The main tube 80 may be made from a suitable metal or plastic, as desired. The main tube 80 has a longitudinal central axis 82 (FIGS. 3 and 5) which forms a longitudinal central axis of the surgical instrument 10. A central passage 84 extends axially along the length of the main tube 80. A proximal end portion 86 (FIG. 1) of the main tube 80 is fixed to the handle 12.

The rigid stem section 20 includes an interface element 90 (FIG. 5) fixed to a distal end portion 92 of the main tube 80. The interface element 90 has a disc-shaped main body portion 94. Upper and lower pairs of deflection control wire passages 100 and 102 (only one of each pair is shown) extend axially through a radially outer section of the main body portion 94 of the interface element 90.

A spring pocket 106 is formed in the main body portion 94 of the interface element 90. The spring pocket 106 has a cylindrical configuration centered on the axis 82. The spring pocket 106 faces distally, that is, in a direction away form the handle 12.

A rib 108 is located on the distal end face 110 of the main body portion 94 of the interface element 90. The rib 108 is located between the two pairs of control wire passages 100 and 102. The rib 108 has a convex, semi-cylindrical cross sectional configuration extending into and out of the plane of the paper as viewed in FIG. 3. The semi-cylindrical configuration of the rib 108 provides for bending or pivotal movement of the flexible stem section 24 relative to the rigid stem section 20, only in an upward or downward direction as viewed in FIGS. 1–3.

A hollow tubular stem portion 112 of the interface element 90 extends proximally from the main body portion 94 of the interface element. The stem portion 112 of the interface element 90 extends inside the central passage 84 in the main tube 80.

The flexible stem section 24 of the surgical instrument 10 includes a plurality of relatively pivotable vertebrae or links 120–129 arranged between the interface element 90 and the surgical tool 30. In the illustrated embodiment, ten identical vertebrae 120–129 are provided. The number of vertebrae can differ, depending on the desired length and amount of bending movement of the flexible stem section 24.

Each one of the vertebrae 120–129 has an annular, disc-shaped main body portion 130 (FIG. 5) generally similar in configuration to the main body portion 94 of the interface element 90. A cylindrical spring passage 132, centered on the axis 82, extends axially through each one of the vertebrae 120–129. Upper and lower pairs of deflection control wire passages 134 and 136 (only one of each pair is shown) extend axially through a radially outer section of the main body portion 94 of each vertebrae 120–129.

The distal end face of each one of the links 120–129 has a convex, semi-cylindrical rib 138. The ribs 138 on the links 120–129 are identical in configuration and orientation to the rib 108 on the interface element 90. In each one of the links 120–129 the spring passage 132 extends axially through the rib 138. The spring passage 132 widens as it extends distally from the main body portion 130 through the rib 138.

The proximal end face of each one of the links 120–129 has a concave, semi-cylindrical socket 140. Each one of the sockets 140 has a concave configuration adapted to pivotally receive one of the ribs 138.

The links 120–129 are arranged relative to the rigid stem section 20 so that the socket 140 on the most proximal link 120 receives the rib 108 on the interface element 90. The rib 138 on the most proximal link 120 is received in the socket 140 on the next most proximal link 122. In a similar manner, the ribs 138 on each one of the links 122–128 are received in the sockets 140 on the links 123–129, respectively. The rib 138 on the most distal link 129 is received in a socket 142 (FIG. 5) on the fixed part 32 of the surgical tool 30.

All the links 120–129 of the flexible stem section 24 are thus supported on the rigid stem section 20 for pivotal movement relative to the rigid stem section. The surgical tool 30 is supported on the flexible stem section 24 for pivotal movement relative to the flexible stem section and to the rigid stem section 20. The surgical tool 30, as viewed in FIGS. 1–3 and 5, is movable in the plane of the paper.

The fixed jaw 32 (FIG. 3) of the surgical tool 30 has a support portion 160 and a cutting edge 162. A proximally facing spring pocket 154 is formed in the support portion 160 of the fixed jaw 32. A pivot pin 164 is mounted in the support portion 160 of the fixed jaw 32.

The movable jaw 34 of the surgical tool 30 is supported on the pivot pin 164 for pivotal movement relative to the fixed jaw 32 about the pivot pin. The movable jaw 34 has a cutting edge 166 which is engageable with the cutting edge 162 of the fixed jaw 32 upon pivotal movement of the movable jaw from the open position shown in FIG. 2 to the closed position shown in FIG. 3.

The flexible stem section 24 includes an extension spring 150 for transmitting axial load between the surgical tool 30 and the rigid stem section 20 of the surgical instrument 10.

The extension spring 150 is made from a suitable material, preferably stainless steel. In the illustrated embodiment, the extension spring 150 is a coiled spring, specifically, a cylindrical helical spring, made from metal wire having a circular cross section. The extension spring 150 is in a free or unstressed condition when the flexible stem section 24 is in a linear condition as shown in FIG. 3. When the extension spring 150 is in a free or unstressed condition, the coils of the spring are in abutting engagement along the length of the spring, and the spring is not compressible axially.

A first end portion 152 (FIG. 5) of the extension spring 150 is located in the spring pocket 154 in the fixed jaw 32 of the surgical tool 30. The extension spring 150 extends through the respective spring passages 132 in the stacked vertebrae 120–129, along the entire length of the flexible stem section 24. A second end portion 156 of the extension spring 150 is located in the spring pocket 106 in the interface element 90 of the rigid stem section 20.

The surgical instrument 10 includes upper and lower deflection control wires 170 and 172 for controlling bending movement of the flexible stem section 24. Each one of the wires 170 and 172 is formed as a U-shaped loop having its ends connected to the deflection control lever 70 and its center looped around the fixed jaw 32 of the surgical tool 30. The proximal ends of the deflection control wires 170 and 172, are connected for movement with the deflection control lever 70. The deflection control wires 170 and 172 extend from the deflection control lever 70 over the tensioner 74 (FIG. 1) and into the central passage 84 in the main tube 80. The tensioner 74 maintains an appropriate amount of tension on the deflection control wires 170 and 172.

The deflection control wires 170 and 172 pass through the rigid stem section 20 into the interface element 90. The deflection control wires 170 and 172 extend through the control wire passages 100 and 102 in the interface element 90, and into the control wire passages 134 and 136 in the links 120–129 of the flexible stem section 24. Central portions 174 and 176 (FIG. 3) of the deflection control wires 170 and 172 are looped around the support portion 160 of the fixed jaw 32 of the surgical tool 30.

The surgical instrument 10 includes an actuator cable 180 for effecting pivotal movement of the movable jaw 34 relative to the fixed jaw 32. The actuator cable 180 is a flexible metal cable having a first end portion 182 (FIG. 3) fixed to the movable jaw 34. The actuator cable 180 extends from the movable jaw 34 into the first end portion 152 of the extension spring 150. The actuator cable 180 extends for the entire length of the extension spring 150 and then into the stem portion 112 of the interface element 90. The dimensions of the extension spring 150 and the actuator cable 180 are selected so that the actuator cable is freely slidable axially within the extension spring but is constrained from radial movement within the extension spring. (The inner diameter of the extension spring 150 is exaggerated for clarity, in some of the Figures.)

An actuator cable guide tube 184 is received in a recess 186 in the proximal end of the stem portion 112 of the interface element 90. The actuator cable guide tube 184 has a hollow, tubular configuration centered on the axis 82 and defining a cable passage 188. The actuator cable 180 extends from the extension spring 150 into the actuator cable guide tube 184. The inner diameter of the guide tube 184 is selected so that the actuator cable 180 is freely slidable axially within the passage 188 in the guide tube but is constrained from radial movement within the guide tube.

A proximal end portion 190 (FIG. 1) of the actuator cable guide tube 184 extends out of the proximal end portion 86 of the main tube 80 and is secured in the handle 12. The actuator cable 180 extends from the guide tube 184 and is secured to the trigger 60 in a manner not shown.

The flexible stem section 24 of the surgical instrument 10 can be bent to a plurality of different orientations relative to the longitudinal axis 82. The rib 108 on the interface element 90 acts as a fulcrum about which the flexible stem section 24 of the surgical instrument 10 is bendable. The surgical instrument 10 bends because of tension on one or the other of the deflection control wires 170 and 172, when the deflection control lever 70 is moved.

The end portions 174 and 176 of the deflection control wires 170 and 172 (FIG. 1) are connected with the deflection control lever 70 in a manner so that pivotal movement of the control lever in a first direction relative to the handle tensions the upper wire 170 and releases tension on the lower wire 172. Pivotal movement of the control lever 70 in a second direction, opposite to the first direction, releases tension on the upper wire 170 but tensions the lower wire 172.

For example, movement of the manually engageable portion of the deflection control lever 70 in a downward direction as viewed in FIG. 1 results in tensioning of the upper deflection control wire 170 and release of tension on the lower control wire 172. The flexible stem section 24 of the instrument 10 bends upward, as shown in FIG. 2.

Conversely, movement of the manually engageable portion of the deflection control lever 70 in an upward direction (not shown) as viewed in FIG. 1 results in tensioning of the lower deflection control wire 172 and release of tension on the upper control wire 170. The flexible stem section 24 of the instrument 10 bends downward.

The amount of bending of the flexible stem section 24 of the surgical instrument 10 is controlled by the amount of tension on the deflection control wires 170 and 172. This is controlled by the amount of movement of the deflection control lever 70 relative to the handle 12. It should be understood that the present invention is not limited to bending movement of, for example, 90° or more. Thus, the flexible stem section 24 might be independently bendable at, say, 18° at each of ten different locations along its length, thus providing a total of 180° of bending movement.

The surgical instrument 10 may be used in association with a cannula or other tubular member (not shown) which is used, in a known manner, to provide an open path through body tissue to an operating site. Once the cannula is properly positioned, the surgical instrument 10 is inserted axially through the cannula until at least the surgical tool 30 protrudes from the distal end of the cannula. A predetermined amount of the flexible stem section 24 of the surgical instrument 10 may also protrude from the distal end of the cannula. When the surgical instrument 10 is thus inserted through the cannula, and the deflection control lever 70 is moved, the flexible stem section 24 of the surgical instrument is bendable at about the location of the distal end of the cannula, to position the surgical tool 30 in the desired location. The distal end of the cannula acts as a fulcrum about which the flexible stem section 24 of the surgical instrument 10 bends. Depending on how much of the surgical instrument 10 protrudes from the distal end of the cannula, the surgical instrument bends through different arcuate paths of different lengths, at different locations along the length of the movable stem section 24.

When the trigger 60 is pulled, the actuator cable 180 is tensioned. The tensile force on the actuator cable 180 is transmitted into the movable jaw 34 and causes the movable jaw to pivot from the open position shown in FIG. 2 to the closed position shown in FIG. 3. The movable jaw 34 moves relative to the fixed jaw 32 and relative to the flexible stem section 24.

The force transmitted by the actuator cable 180 places an axial load on the fixed jaw 32 of the surgical tool 30. The fixed jaw 32, and thus the surgical tool 30 as a whole, is urged in a direction toward the rigid stem section 20. This pulling force on the surgical tool 30 is transmitted through the fixed jaw 32 to the first end portion 152 of the extension spring 150. The axial force on the extension spring 150 holds the first end portion 152 of the extension spring in the spring pocket 154 in the fixed jaw 32. The first end portion 152 of the extension spring 150 is, effectively, fixed for movement with the fixed jaw 32.

The axial compressive force on the extension spring 150 is transmitted through the second end portion 156 of the extension spring into the rigid stem section 20. The compressive force on the extension spring 150 holds the second end portion 156 of the extension spring in the spring pocket 158 in the interface element 90. The second end portion 156 of the extension spring 150 is, effectively, fixed for movement with the rigid stem section 20.

The length of the extension spring 150 is selected so that the extension spring carries substantially all axial load between the surgical tool 30 and the rigid stem section 20. Thus, there is no substantial axial load transmitted through any of the vertebrae 120–129. The only significant axial load on the vertebrae 120–129 comes from the force of the deflection control wires 170 and 172. The vertebrae 120–129 are supported on each other, but only lightly, so as to enable free bending movement of the flexible stem section 24 even when there is a large axial load being directed from the tool through the flexible stem section to the handle 12. As a result, the flexible stein section 24 can bend relatively freely. Also, the links 120–129 can be made from a lighter and/or less expensive material.

From the above description of the invention, those skilled in the art will perceive improvements, changes and modifications in the invention. For example, the surgical instrument 10 can include a different type of surgical tool which has a movable part and a fixed part. Such improvements, changes and modifications within the skill of the art are intended to be covered by the appended claims.

Having described the invention, we claim:

1. A surgical instrument comprising:

a handle;

a rigid stem section extending from said handle;

a flexible stem section extending from said rigid stem section;

a surgical tool connected with a distal end of said flexible stem section, said surgical tool including a movable part;

said flexible stem section comprising a plurality of relatively pivotable vertebrae extending along said flexible stem section and an extension spring extending axially through said plurality of vertebrae, said extension spring transmitting substantially all axial load between said surgical tool and said rigid stem section, said flexible stem section being freely bendable even when there is a large axial load being transmitted through said flexible stem section between said surgical tool and said rigid stem section; and an actuator cable extending through said extension spring and connected with said movable tool part for applying force to said movable tool part to move said movable part relative to said flexible stem section.

2. An instrument as set forth in claim 1 wherein said extension spring is a coil spring having opposite first and second end portions, said first end portion of said extension spring engaging said surgical tool and said second end portion of said extension spring engaging said rigid stem section.

3. An instrument as set forth in claim 2 wherein said first and second end portions of said spring are received in respective spring pockets in said surgical tool and said rigid stem section.

4. An instrument as set forth in claim 1 comprising at least one deflection control wire for moving said flexible stem section between a plurality of orientations relative to said rigid stem section, said wire extending through said vertebrae, said wire applying an axial load on said surgical tool to urge said fixed tool part toward said rigid stem section thereby placing an axial compressive load on said extension spring.

5. A surgical instrument as set forth in claim 4 wherein said actuator cable and said extension spring bend during movement of said flexible stem section and said surgical tool between said plurality of orientations.

6. An instrument as set forth in claim 1 wherein said extension spring is in a free or unstressed condition in which the coils of said spring are in abutting engagement along the length of said spring and said spring is not compressible axially, when said flexible stem section is in a linear condition.

7. An instrument as set forth in claim 1 wherein said actuator cable comprises a flexible member which extends for the entire length of said extension spring and which is connected with a manually engageable member on said handle, said manually engageable member on said handle being movable to transmit force through said actuator cable for moving said movable tool part relative to said flexible stem section.

8. A surgical instrument as set forth in claim 1 wherein the distal end face of said rigid stem section has a curved surface for supporting said plurality of vertebrae for bending movement relative to said rigid stem section.

9. A surgical instrument as set forth in claim 1 wherein each one of said plurality of relatively pivotable vertebrae has an annular, disc-shaped main body portion, a distal end face having a convex, semi-cylindrical rib, and a proximal end face having a convex configuration adapted to pivotally receive one of said convex, semi-cylindrical ribs.

* * * * *